(12) United States Patent
Honaryar

(10) Patent No.: US 8,858,421 B2
(45) Date of Patent: Oct. 14, 2014

(54) INTERIOR NEEDLE STICK GUARD STEMS FOR TUBES

(75) Inventor: Babak Honaryar, Orinda, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 241 days.

(21) Appl. No.: 13/296,634

(22) Filed: Nov. 15, 2011

(65) Prior Publication Data

US 2013/0123573 A1    May 16, 2013

(51) Int. Cl.
| | | |
|---|---|---|
| *A61F 2/02* | (2006.01) | |
| *A61F 2/04* | (2013.01) | |
| *A61M 39/02* | (2006.01) | |
| *A61M 39/04* | (2006.01) | |
| *A61M 39/10* | (2006.01) | |
| *A61F 5/00* | (2006.01) | |

(52) U.S. Cl.
CPC .......... *A61F 5/0056* (2013.01); *A61M 39/0208* (2013.01); *A61M 2039/1066* (2013.01); *A61M 2039/0226* (2013.01)
USPC ........................................................ 600/37

(58) Field of Classification Search
CPC . A61M 39/04; A61M 39/10; A61M 39/0208; A61M 2039/0282; A61M 2039/1066; A61F 5/0056
USPC ................... 600/37; 604/288.01–288.04, 175
See application file for complete search history.

(56) References Cited

U.S. PATENT DOCUMENTS

| | | |
|---|---|---|
| 586,113 A | 7/1897 | Bott |
| 2,163,048 A | 6/1939 | McKee |
| 2,737,954 A | 3/1956 | Knapp |
| 3,371,352 A | 3/1968 | Siposs et al. |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Helioscopie Product Insert for Heliogast, pp. 1-11 (undated).

(Continued)

*Primary Examiner* — Charles A Marmor, II
*Assistant Examiner* — Thaddeus Cox
(74) *Attorney, Agent, or Firm* — Gordon & Jacobson, PC

(57) ABSTRACT

Generally described herein are apparatus, systems and methods related to a stem insertable into the access port tubing for the prevention of fluid leaks. More particularly, the stem or stems may be larger than the interior diameter of the access port tubing thereby providing a fluid seal to keep the fluid within the access port tubing. However, these fluid seals might not be absolute and may still allow a certain degree of leakage. In one embodiment, by including barbs which further presses against the interior diameter of the access port tubing, the sealing of the fluid may be substantially improved. The stem itself, while impenetrable by a needle, may still allow for bend flexibility of the access port tubing by employing a ball and socket joint for connecting to a next stem. In this manner, fluid leak prevention is improved while retaining the mobility of the access port tubing.

21 Claims, 6 Drawing Sheets

(56) References Cited

U.S. PATENT DOCUMENTS

| | | |
|---|---|---|
| 3,688,764 A | 9/1972 | Reed |
| 3,840,018 A | 10/1974 | Heifetz |
| 3,958,562 A | 5/1976 | Hakim et al. |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Showell et al. |
| 4,161,943 A | 7/1979 | Nogier |
| 4,164,943 A | 8/1979 | Hill et al. |
| 4,190,040 A | 2/1980 | Schulte |
| 4,233,992 A | 11/1980 | Bisping |
| 4,265,252 A | 5/1981 | Chubbuck et al. |
| 4,280,722 A | 7/1981 | Guptil et al. |
| 4,413,985 A | 11/1983 | Wellner et al. |
| 4,474,572 A | 10/1984 | McNaughton et al. |
| 4,502,335 A | 3/1985 | Wamstad et al. |
| 4,543,088 A | 9/1985 | Bootman et al. |
| 4,557,722 A | 12/1985 | Harris |
| 4,569,675 A | 2/1986 | Prosl et al. |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A | 6/1987 | Fenton, Jr. et al. |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A | 9/1988 | Wiita et al. |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A | 6/1989 | Hancock et al. |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A | 12/1989 | Johnston et al. |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,156,792 A * | 10/1992 | Holdaway et al. ............ 264/230 |
| 5,167,638 A | 12/1992 | Felix et al. |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A | 12/1997 | Flaherty et al. |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,270,475 B1 | 8/2001 | Bestetti et al. |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |

(56) References Cited

U.S. PATENT DOCUMENTS

| | | |
|---|---|---|
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze et al. |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon et al. |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,530,943 B2 | 5/2009 | Lechner |
| 7,553,298 B2 | 6/2009 | Hunt et al. |
| 7,561,916 B2 | 7/2009 | Hunt et al. |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum et al. |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 | 10/2010 | Birk et al. |
| 7,850,660 B2 | 12/2010 | Uth et al. |
| 7,862,546 B2 | 1/2011 | Conlon et al. |
| 7,909,754 B2 | 3/2011 | Hassler, Jr. et al. |
| 7,909,804 B2 | 3/2011 | Stats |
| 8,007,474 B2 | 8/2011 | Uth et al. |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyer |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon et al. |
| 2005/0131383 A1 | 6/2005 | Chen et al. |
| 2005/0148956 A1 | 7/2005 | Conlon et al. |
| 2005/0149143 A1 | 7/2005 | Libbus et al. |
| 2005/0209573 A1 | 9/2005 | Brugger et al. |
| 2005/0240155 A1 | 10/2005 | Conlon |
| 2005/0240156 A1 | 10/2005 | Conlon |
| 2005/0267500 A1 | 12/2005 | Hassler, Jr. et al. |
| 2005/0277899 A1 | 12/2005 | Conlon et al. |
| 2005/0283041 A1 | 12/2005 | Egle |
| 2005/0283118 A1 | 12/2005 | Uth et al. |
| 2005/0283119 A1 | 12/2005 | Uth et al. |
| 2006/0074439 A1 | 4/2006 | Garner et al. |
| 2006/0122578 A1 | 6/2006 | Lord et al. |
| 2006/0161186 A1 | 7/2006 | Hassler, Jr. et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk et al. |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1 | 9/2006 | Schulze et al. |
| 2006/0235445 A1 | 10/2006 | Birk et al. |
| 2006/0235448 A1 | 10/2006 | Roslin et al. |
| 2006/0247539 A1 | 11/2006 | Schugt et al. |
| 2006/0264898 A1* | 11/2006 | Beasley et al. ............... 604/506 |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |
| 2007/0016231 A1 | 1/2007 | Jambor et al. |
| 2007/0027356 A1 | 2/2007 | Ortiz |
| 2007/0038255 A1 | 2/2007 | Kieval et al. |
| 2007/0060959 A1 | 3/2007 | Salo et al. |

(56) References Cited

U.S. PATENT DOCUMENTS

| | | |
|---|---|---|
| 2007/0073250 A1 | 3/2007 | Schneiter |
| 2007/0078391 A1 | 4/2007 | Wortley et al. |
| 2007/0088336 A1 | 4/2007 | Dalton |
| 2007/0088391 A1 | 4/2007 | McAlexander et al. |
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon et al. |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe et al. |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin et al. |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |
| 2011/0196195 A1 | 8/2011 | Raven et al. |
| 2011/0270019 A1* | 11/2011 | Deuel et al. .................. 600/37 |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |
| WO | WO 99/20338 | 4/1999 |

(56) References Cited

FOREIGN PATENT DOCUMENTS

| | | |
|---|---|---|
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/10667 | 2/2002 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

http://en/wildpedia.org/Injection_Molding.

* cited by examiner

INTERIOR NEEDLE STICK GUARD STEMS FOR TUBES

FIELD

The present invention generally relates to medical systems, devices and uses thereof for treating obesity and/or obesity-related diseases. More specifically, the present invention relates to one or more stems for guarding against needle sticks as related to an access port used as a part of a gastric banding system implantable in a patient.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Over time, a stoma created by a gastric band may need adjustment in order to maintain an appropriate size, which is neither too restrictive nor too passive. Accordingly, prior art gastric band systems provide a subcutaneous fluid access port ("access port") connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Typically, the access port, and in particular, the tubing leading from the access port to a reservoir or the inflatable portion of the gastric band may be susceptible to a misdirected needle. That is, a misdirected needle may puncture the tubing and cause leaking of fluid out of the gastric banding system, which may eventually lead to reduced efficacy of the gastric band. In some scenarios, the entire gastric banding system may then need to be removed from the body or the physician may need to perform an operation to mend the punctured tube.

Exterior tubing shields have been used as one option to protect the tubing from puncturing from stray needles. However, tubing shields add bulk, which may in certain patients, reduce the biocompatibility of the tubing and/or reduce the comfort of the gastric banding system within the patient.

What is needed is an interior tubing protection system that can reduce the likelihood and/or severity of leaking while still maintaining the relatively less bulky tubing currently incorporated in gastric banding systems.

SUMMARY

Generally described herein are apparatus, systems and methods related to a stem insertable into the access port tubing for the prevention of fluid leaks. More particularly, the stem or stems may be larger than the interior diameter of the access port tubing thereby providing a fluid seal to keep the fluid within the access port tubing. However, these fluid seals might not be absolute and may still allow a certain small degree of leakage. In one embodiment, by including barbs which further press against the interior diameter of the access port tubing, the sealing of the fluid may be substantially improved. The stem itself, while impenetrable by a needle under normal application of force, may still allow for bend flexibility of the access port tubing by employing a ball and a socket joint for connecting to a next stem. In this manner, fluid leak prevention is improved while retaining the mobility of the access port tubing.

In one embodiment, provided is an access port for use with a gastric band for the treatment of obesity. The access port may comprise a housing enclosing a fluid reservoir, a conduit having a first end connected to the fluid reservoir and a bulbous second end, a tube having an inner surface defining a first pathway, a first end connected to the bulbous second end of the conduit and a second end connected to an inflatable portion of the gastric band. The tube further having a first stem guard located within the first pathway of the tube and configured to prevent a first needle from passing therethrough. The first stem guard may further include a first socket-shaped tail portion for receiving the bulbous second end of the conduit, a first ball-shaped head portion, a first shaft portion located between the first socket-shaped tail portion and the first ball-shaped head portion, the first shaft portion defining a second pathway for carrying fluid, and a first barb portion protruding from the first shaft portion and configured to extend into the inner surface of the tube.

In one embodiment, provided is a flexible tubing for carrying fluid between an access port and an inflatable portion of a gastric band. The flexible tubing may comprise a body configured to have a first end attachable to a bulbous end of a conduit of the access port and a second end attachable to the inflatable portion, the body having an inner surface defining a first pathway for carrying fluid, and a first stem guard located within the first pathway of the body and configured to prevent a needle from passing therethrough. The first stem guard may further include a first socket-shaped tail portion for receiving a bulbous second end of the conduit, a first ball-shaped head portion, a first shaft portion located between the first socket-shaped tail portion and the first ball-shaped head portion, the first shaft portion defining a second pathway for carrying fluid, and a first barb portion protruding from the first shaft portion and configured to extend into the inner surface of the body.

In one embodiment, provided is a needle stem guard located internally within a first pathway of a flexible tubing for the prevention of leaks. The needle stem guard may comprise a socket-shaped tail portion for receiving a bulbous conduit connected to a fluid reservoir of an access port, a ball-shaped head portion, a shaft portion located between the first socket-shaped tail portion and the ball-shaped head portion, the shaft portion defining a second pathway for carrying fluid, and a barb portion protruding from the shaft portion.

BRIEF DESCRIPTION OF THE DRAWINGS

The features, obstacles, and advantages of the present invention will become more apparent from the detailed description set forth below when taken in conjunction with the drawings, wherein.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

Figure 1:
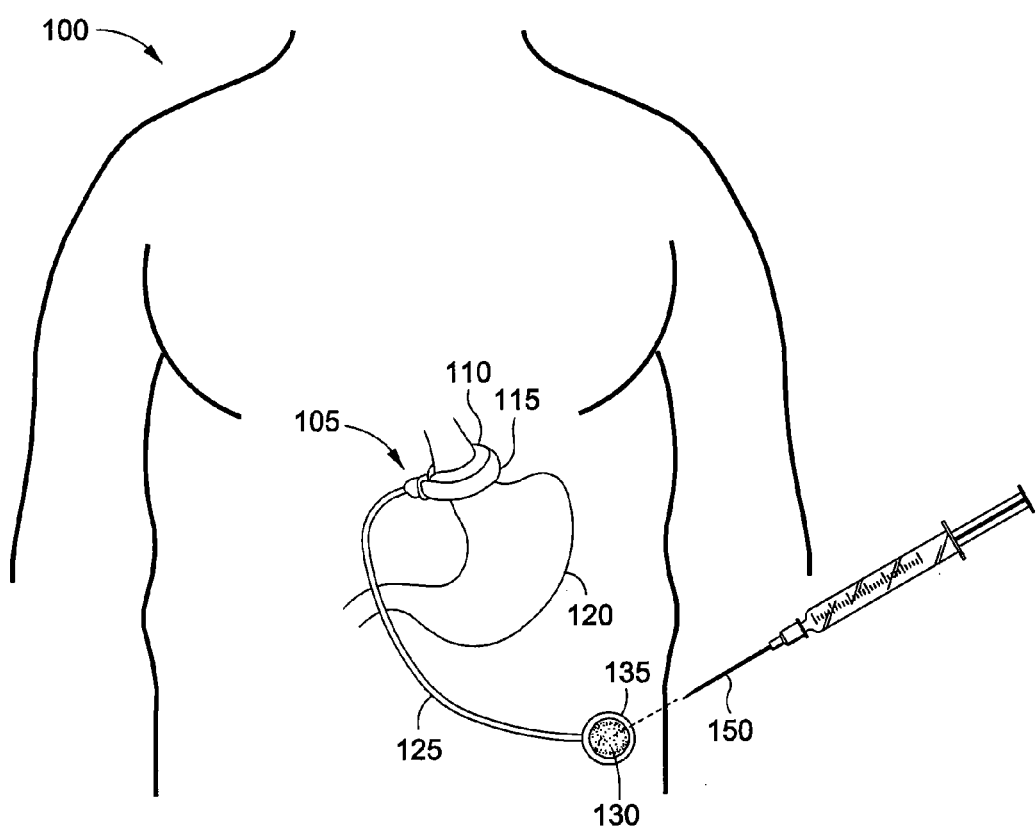
FIG. 1 illustrates a gastric banding system including an access port according to an embodiment of the present invention.

FIG. 1 illustrates an implantable gastric banding system 105 used for the treatment of obesity. In the embodiment shown, a tube 125 and an access port 130 are used in the implantable gastric banding system 105, including a gastric band 110 configured to form a loop around a portion of a stomach 120 of a patient 100 to form a stoma. The gastric band 110 is preferably wrapped around the cardia or esophageal junction of the stomach 120 to restrict the flow of food passing from the upper portions of the stomach 120 to the lower portions of the stomach 120. The restricted flow of food enhances the satiety signals sensed by the patient 100, which desirably reduces food consumption of the patient 100, which aids the patient 100 in losing weight.

Over time, a physician may need to adjust the degree to which the gastric band 110 constricts the stomach. As such, the gastric band 110 may include an inflatable portion 115, which comprises an inflatable cuff that wraps around the stomach 120 of the patient 100. The inflatable portion 115 may be filled with fluid. The amount of fluid in the inflatable portion 115 defines the degree to which the gastric band 110 constricts the stomach 120 (e.g., a greater amount of fluid in the inflatable portion 115 will increase the constriction of the stomach 120). A physician may adjust the amount of fluid in the inflatable portion 115 via the access port 130.

The access port 130 is preferably fixed subcutaneously within the body of the patient 100, and is preferably fixed to body tissue including the interior muscle wall of the patient 100. The tube 125 conveys fluid to and from the inflatable portion 115 via the access port 130. One end of the tube 125 couples to the access port 130, and the other end of the tube 125 couples to the inflatable portion 115 of the gastric band 110.

A physician inserts a syringe needle 150 into the patient's body to access the access port 130, and varies the amount of fluid in the inflatable portion 115 of the gastric band 110. Generally, the physician must attempt to locate a septum 135 of the access port 130 to pass the syringe 150 needle through the septum 135. The septum 135 must be penetrated by the syringe needle 150 to allow fluid to enter, or be removed from the access port 130. The physician will typically palpate the area around the access port 130 to locate the septum 135.

However, it may be difficult for the physician to properly locate the septum 135, because the access port 130 may be covered by many layers of skin and/or fat. Accordingly, it is possible the physician may not properly locate the septum 135, and may insert the syringe 150 needle in the wrong location. The physician may errantly contact a portion of the tube 125 proximal to the access port 130. The syringe needle 150 may puncture the tube 125, specifically the end of the tube 125 connected to the access port 130, and may cause fluid to leak from the gastric banding system 105. A surgical procedure may be necessary to repair the punctured tube 125, or replace the entire gastric banding system 105.

By incorporating an apparatus to guard the tube 125 from leaking fluid, this undesirable result may be avoided or prevented.

Figure 2A:
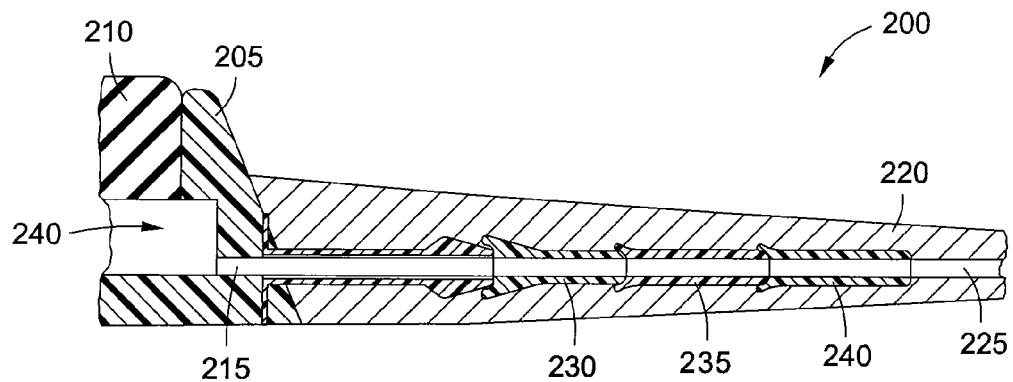
FIG. 2A illustrates needle stick stem guards without barbs according to an embodiment of the present invention.

FIG. 2A illustrates an access port system 200 having needle stick guard stems 230, 235, 240 deployed or positioned in an internal fluid pathway 225 to prevent the leaking out of fluid when a needle pricks or penetrates a flexible tubing 220 between an access port 205 and a gastric band (not shown). As shown, the needle stick guard stem 230 is connected to an access port connector 215, which in turn, serves as a fluid conduit between an internal fluid reservoir 240 of the access port 205 and the rest of the gastric band. The needle stick guard stem 230 is attached to another needle stick guard stem 235, which in turn is attached to the needle stick guard stem 240. As these needle stick guard stems 230, 235, 240 are positioned inside the internal fluid pathway 225, in one sense, they block or restrict the internal fluid pathway 225. However, the needle guard stems 230, 235 and 240 include stem portions that are hollowed out to serve as fluid conduits while protecting the hollow interior from leakage caused by needle puncturing. In essence, the needle guard stems 230, 235 and 240 are able to fluidly couple the internal fluid reservoir 240 and the internal fluid pathway 225 by creating a substitute fluid pathway to allow fluid to travel from the fluid reservoir 240 to the internal fluid pathway 225, and vice versa.

Advantageously, by utilizing a plurality of short needle stick guard stems (as opposed to one long one), flexibility of the tubing 220 may be maintained. As shown, the needle stick guard stem 240 leads to unprotected portions of the internal fluid pathway 225. In practice, because physicians attempting to penetrate a septum 210 of the access port 205 are unlikely to miss by more than a few inches, additional needle stick guard stems may not be necessary. However, additional needle stick guard stems may be employed if desired.

Generally, the needle stick guard stems may prevent the needle from directly penetrating its shell and creating a large leak. However, the fact that these needle stick guard stems mainly incorporate physical pressure (e.g., pressing against and/or slightly stretching the outer diameter of the internal fluid pathway 225) to provide sealing renders the needle stick guard stems susceptible to allowing leaks from the joints (i.e., the connection point between two adjacent needle stick stem guards).

Figure 2B:
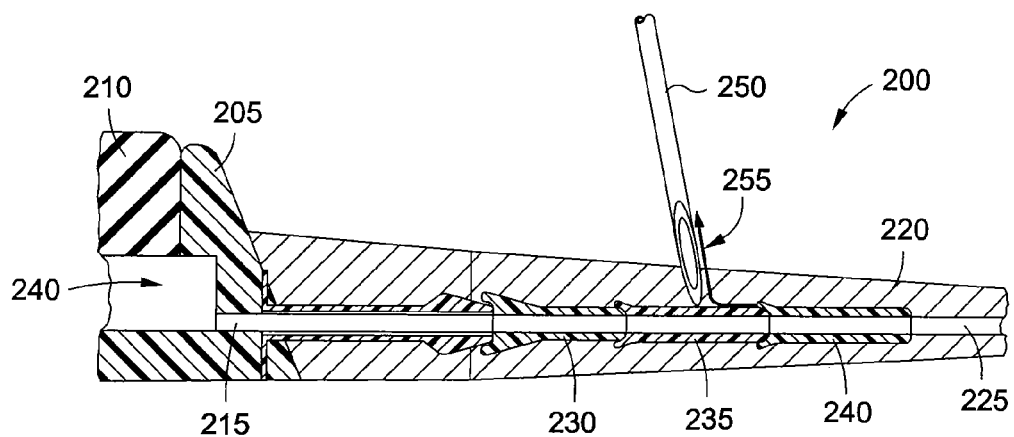
FIG. 2B illustrates a potential leak path utilizing the needle stick stem guards without barbs of FIG. 2A.

FIG. 2B illustrates examples of a potential leakage path 255 and which may result when a misdirected needle 250 penetrates the area proximal to the stem. This potential leakage path 255 may allow fluid inside the gastric banding system to undesirably leak out potentially reducing the efficacy of the gastric banding system.

Accordingly, one or more barbs may be employed to prevent fluid passage from the joint to a puncture hole caused by a misdirected needle. FIGS. 3A-3H illustrates an embodiment having needle stick stem guards that are less susceptible to allowing leaks from joints.

Figure 3A:
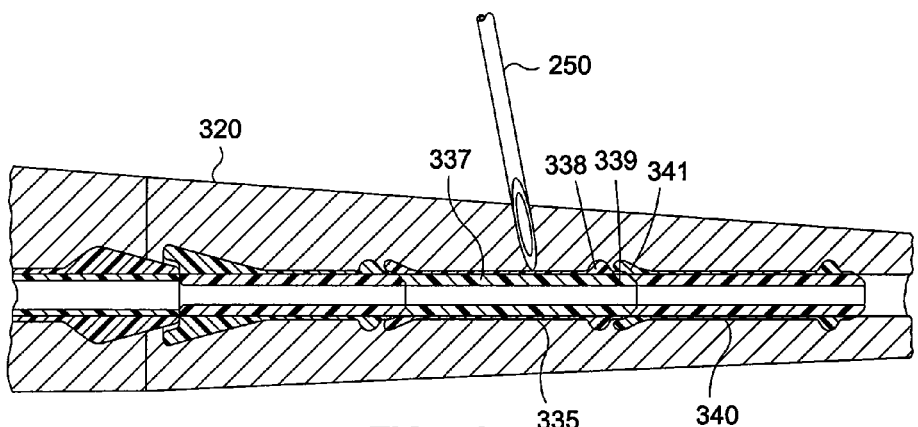
FIG. 3A illustrates how the inclusion of barbs to needle stick stem guards may prevent a potential leak path according to an embodiment of the present invention.

FIG. 3A illustrates a similar scenario as FIG. 2B, where the misdirected needle 250 penetrates the area proximal to a needle stick guard stem 335. However, due to the presence of a barb or protrusion 338, fluid from the joint created by a head portion 339 and a corresponding tail portion 341 is blocked from traveling along the exterior of the needle stick guard stem 335 and out a hole caused by the needle 250. Accordingly, the addition of a barb or protrusion 338 provides an advantageous benefit of leak prevention.

Figure 3B:
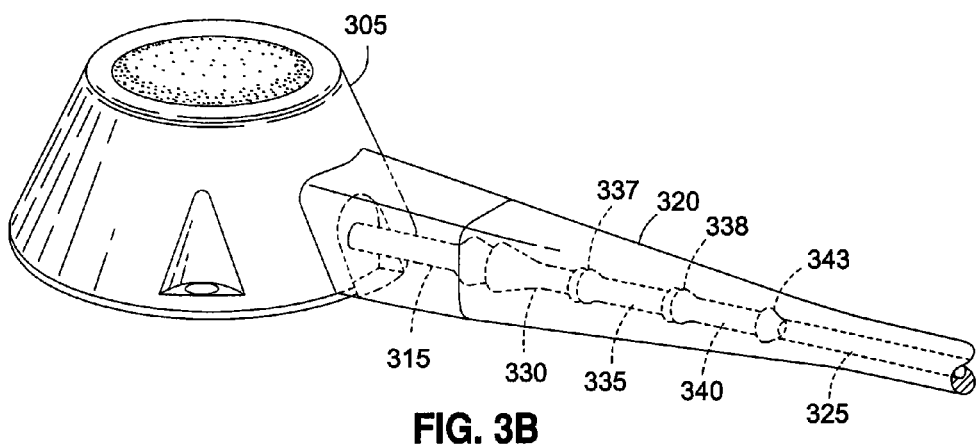
FIG. 3B illustrates needle stick stem guards with barbs according to an embodiment of the present invention.

FIG. 3B illustrates a perspective view of a portion of a gastric banding employing the features of FIG. 3A. Here, needle stick guard stems 330, 335, 340 deployed or positioned in an internal fluid pathway 325 to prevent the fluid from leaking out of the gastric banding system when a needle pricks or penetrates the flexible tubing 320 connecting an access port 305 and a gastric band (not shown). Each of the needle guard stems 330, 335, 340 includes a barb or protrusion portion 333, 338 and 343, respectively, directed to block a portion of the internal fluid pathway 325 in order to prevent fluid passage from a joint to a puncture hole caused by a misdirected needle in a manner similar to the illustration of FIG. 3A and the corresponding description, thereby increasing the leaking prevention capabilities.

In addition, the needle guard stems 330, 335, 340 are slightly larger than the inner diameter of the internal fluid pathway 325 of the flexible tubing 320 and therefore press against the flexible tubing 320 to create a fluid seal.

Figure 3C:
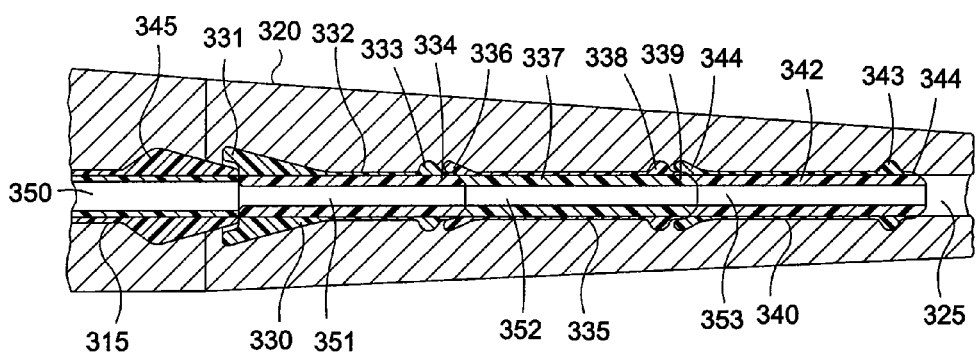
FIG. 3C illustrates a close-up, cross-sectional view of a portion of FIG. 3A according to an embodiment of the present invention.

FIG. 3C illustrates a close up, cross-sectional view of FIG. 3A. As shown from left to right, an access port connector 315 defining a fluid conduit 350 may include a bulbous conduit head 345 connectable to the first needle guard stem 330. More particularly, the head 345 fits into a tail portion 331 of the first needle guard stem 330. The first needle guard stem 330, in addition to the tail portion 331, may include a shaft portion 332, a barb portion 333 and a head 334 portion. The head portion 334 may fit into a tail portion 336 of the second needle guard stem 335 (in a manner that a ball may fit into a socket to create a flexible joint). The second needle guard stem 335 may also include a shaft portion 337, a barb portion 338 and a head portion 339. Similarly, the head portion of 339 of the second needle guard stem 335 fits into a tail portion 341 of the third needle guard stem 340 to create another flexible joint. The third needle guard stem 340 may also include a shaft portion 342, a barb portion 343 and a head portion 344. The stems 332, 337 and 342 may each be molded to include a cavity for transporting fluid, for example, internal fluid pathways 351, 352 and 353 for establishing a fluid path between the fluid conduit 350 and the internal fluid pathway 325.

The addition of barbs 333, 338 and 343 at the joint areas proximal to the location of the heads 334, 338 and 344 are located advantageously to prevent fluid passage from the joint to a punctured hole. That is, the protruding aspects of the bulbous barb act as a shield to block the joint from being penetrated by a misdirected needle. In addition, since the barb portions 333, 338 and 343 significantly bulge out into the inner diameter of the tube, a better fluid seal is provided at the location of the barb portions 333, 338 and 343. In this manner, a leak may be limited to only existing fluid between two adjacent barbs since additional fluid cannot flow past the barbs and out of the puncture hole.

Figure 3D:
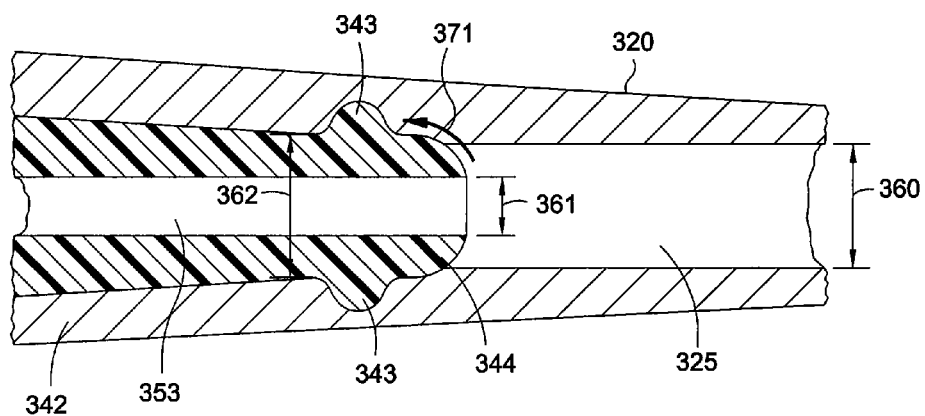
FIG. 3D illustrates an even closer view of a portion of FIG. 3A according to an embodiment of the present invention.

FIG. 3D further illustrate the relative diameters of a needle stick stem guard (e.g., needle stick stem guard 340) which serves to explain how fluid is passed between the fluid paths 325 and 353 while being blocked by barb portion 343 and how a fluid seal is created by a diameter 362 of the needle stick stem guard 340. As shown in FIG. 3C, the inner diameter of a tube 360 may be larger or equal to an inner diameter 361 of the fluid path 353. However, the inner diameter 361 is less than the diameter 362 of the needle stick stem guard 340. In this manner, any leaking of fluid as shown by arrow 371 is minimal. The barb portion 343 further seals and/or blocks the fluid shown by arrow 371 as it protrudes even deeper into the flexible tubing 320. Accordingly, fluid may travel between fluid pathway 325 and 353 without leaking out of the pathway.

Figure 3E:
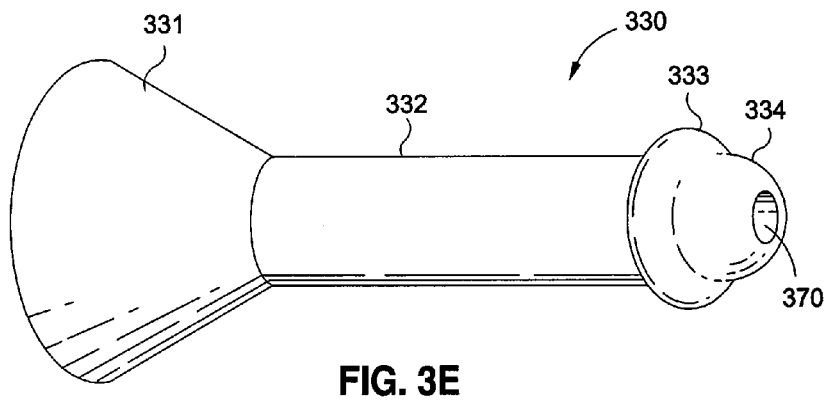
FIG. 3E illustrates a stem guard for attaching to a connector of an access port housing according to an embodiment of the present invention.
Figure 3F:
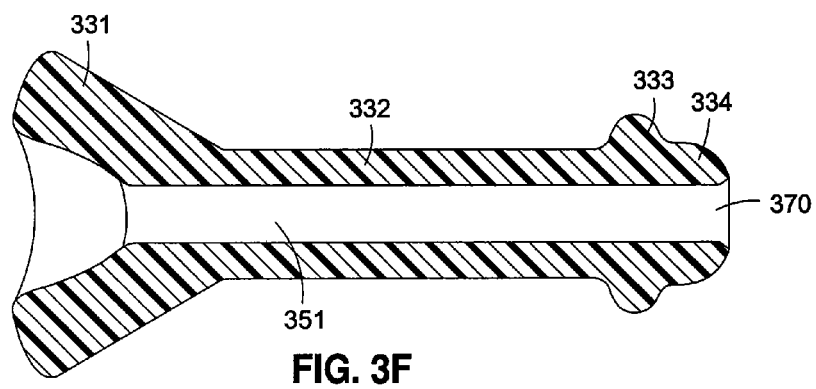
FIG. 3F illustrates a cross-sectional view of the stem guard of FIG. 3E according to an embodiment of the present invention.

FIG. 3E illustrates a close-up view of the first needle stem guard 330 and FIG. 3E illustrates a cross-sectional view of the first needle guard 330. The fluid pathway of the first needle stem guard 351 is hidden from view in FIG. 3D (as it extends from the opening 370 of the head portion to the tail portion 331), but is revealed in FIG. 3E. The first needle stem guard 330 as described above may include the tail portion 331 for receiving the head 345 of the connector 315. At one end, the tail portion 331 may have an opening with a first diameter sized to fit the head portion 345 and may taper down to a relatively smaller diameter corresponding to portion of the shaft portion 332 (which may still be slightly larger than an inner diameter of the fluid pathway, for example, fluid pathway 325). The shaft portion 332 may lead to the barb portion 333 which bulges out beyond the outer diameter of the shaft portion 332. On the other side of the barb portion 333 may be the head portion 334 which includes a hole 370 for allowing fluid to enter and travel along the fluid pathway 351.

In one embodiment, the first needle guard 330 may be anywhere between about 0.5 centimeters to about 5 centimeters long as measured between the head portion 334 and the tail portion 331. Preferably, the first needle stem guard 330 may be between about 2 to 4 centimeters long.

The first needle stem guard 330 may be constructed out of any suitable biocompatible material including, but not limited to, titanium, stainless steel, polysulfone, PPSU, PEEK from Solvay, UHMWPE from Ticona, and any combination thereof.

Figure 3G:
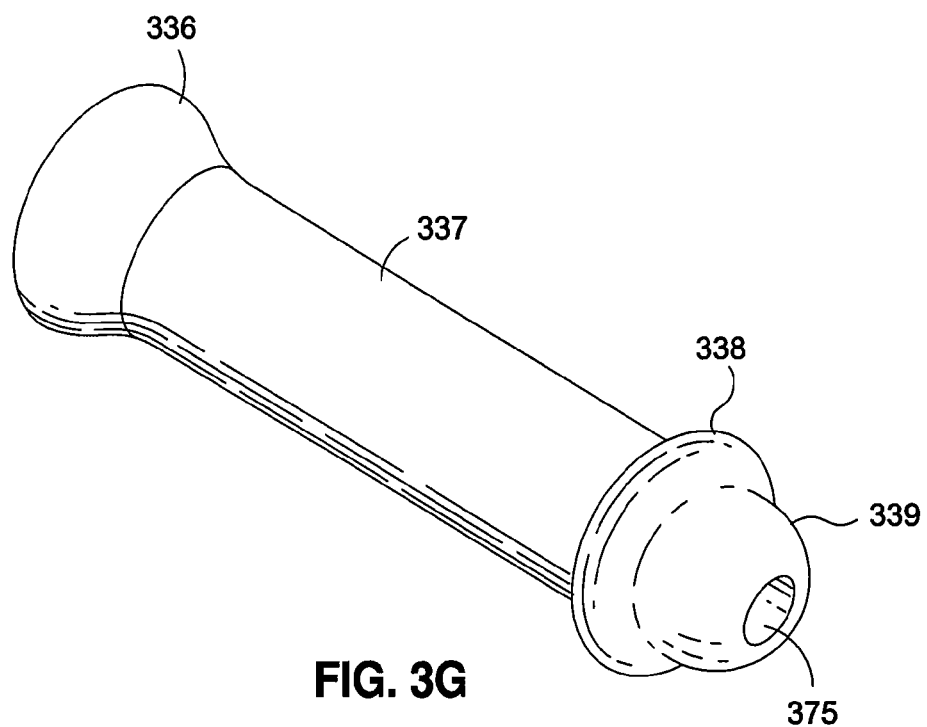
FIG. 3G illustrates a stem guard for attaching to another stem guard according to an embodiment of the present invention.
Figure 3H:
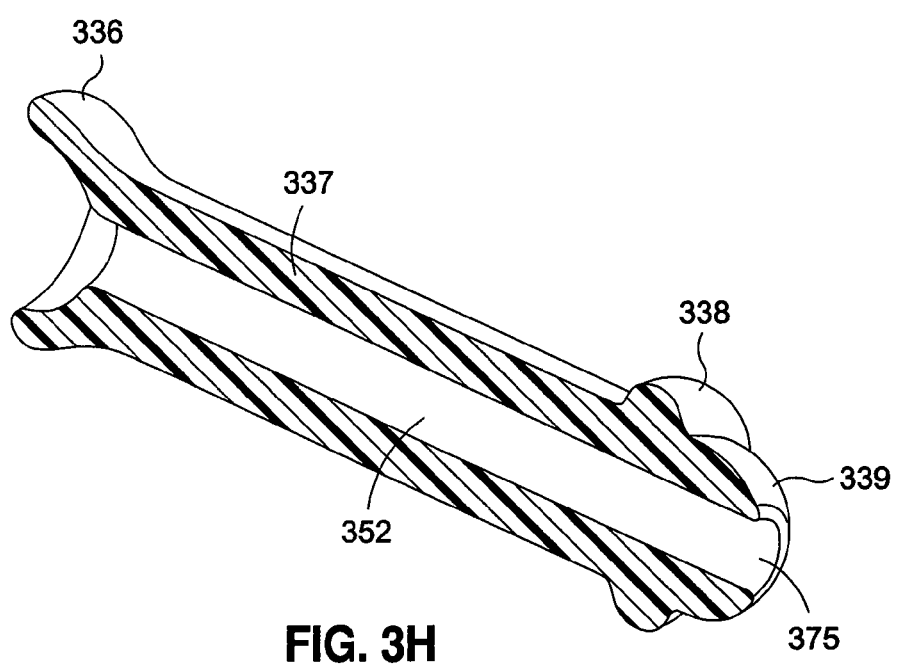
FIG. 3H illustrates a cross-sectional view of the stem guard of FIG. 3G according to an embodiment of the present invention.

FIGS. 3G and 3H illustrate an example of a stem guard other than the first needle stem guard 330 (e.g., stem guard 335 or 340). For ease of understanding, references will be made to the second needle stem guard 335 as attachable to the first needle stem guard 330, but the characteristics are also applicable to the third needle stem guard 340 or any other stem guards that may be desirably added. As compared to the first needle stem guard 330, the second needle stem guard 335 has a tail portion 336 configured to be a different shape and size. The reason for the difference is because the two tails, 331 and 336, respectively, may receive head that are shaped differently. While the tail 331 is shown to be larger to accommodate for the larger connector head 345, other variations are possible (e.g., where the connector head is actually smaller than a head of the stem guards). Indeed, besides the shape and size of the tail portion 336, the second stem guard 335 is virtually identical in size, functionality and material as the first stem guard 330. In other words, the tail portion 336 of the second needle stem guard 375 may have an opening with a first diameter sized to fit the head 334 of the first needle stem guard 330 and may taper down to a relatively smaller diameter corresponding to the portion of the shaft portion 337 (which may still be slightly larger than an inner diameter of the fluid pathway, for example, fluid pathway 325). The shaft portion 337 may lead to the barb portion 338 which bulges out beyond the diameter of the shaft portion 337. On the other side of the barb portion 338 may be the head portion 339 which includes a hole 375 for allowing fluid to enter and travel along the fluid pathway 352 and through the fluid pathway 351 of the first needle stem guard 330. The dimensions of the shaft portion 337, the barb portion 338 and the head portion 339 may, in one embodiment, be identical to the dimensions of the shaft portion 332, the barb portion 333 and the head portion 334 of the first needle stem guard 330. Indeed, identical dimensioning of needle stem guards may allow for cheaper manufacturing and improved compatibility as the needle stem guards all couple to at least one other needle stem guard to produce a protected fluid path.

Furthermore, the shape of the head of one needle stem guard is configured to be received by the shape of the tail of an adjacent needle stem guard in order to provide the "ball-and-socket" functionality and thereby allow pivoting of the respective, adjacent needle stem guards to maintain flexibility of the tubing within which the needle stem guards are positioned.

In newly designed access ports and/or other appropriate access ports, the connector leading out of the access port housing (e.g., the access port connector 315) may be designed to have a head that is shaped and dimensioned similarly to the head of the first needle stem guard, the second needle stem guard, the third needle stem guard, and so forth. By conforming the head shape and dimension of the connector to be the same as the needle stem guards, all needle stem guards may be identical. In other words, this will eliminate the need for the first needle stem guard (e.g., first needle stem guard 335) interfacing with the connector (e.g., connector 315) to include a differently shaped and/or dimensioned tail.

Figure 4A:
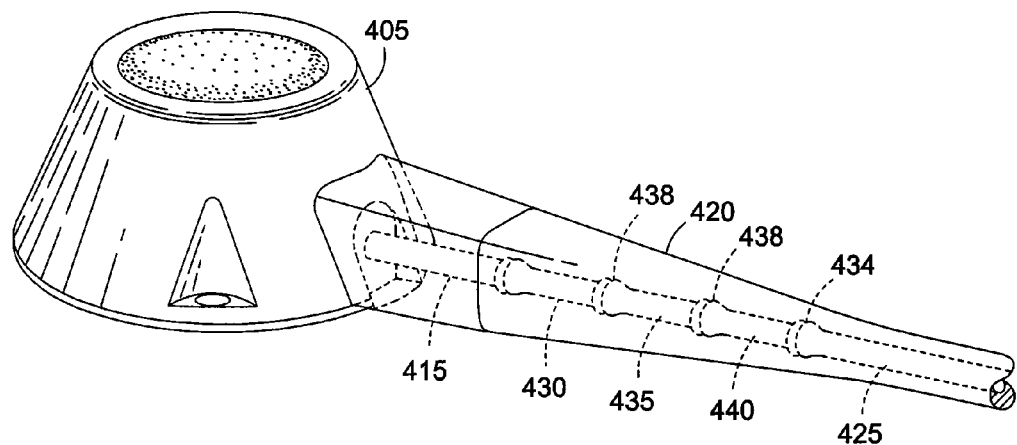
FIG. 4A illustrates needle stick stem guards with barbs according to an embodiment of the present invention.
Figure 4B:
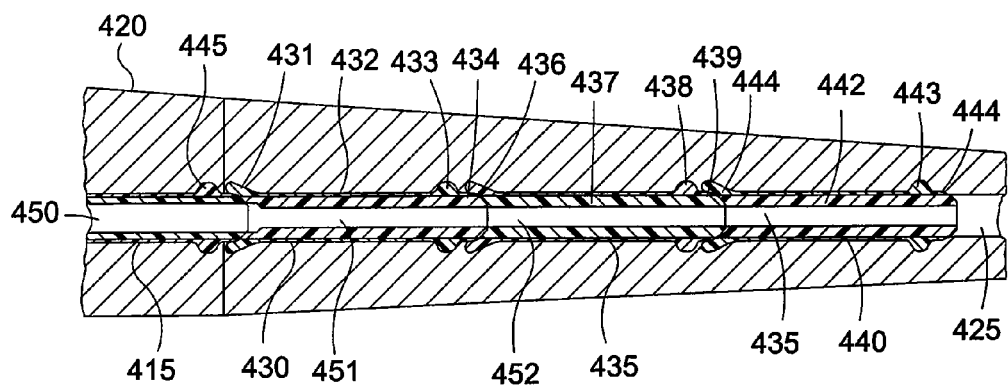
FIG. 4B illustrates a close-up, cross-sectional view of a portion of FIG. 4A according to an embodiment of the present invention.

For example, FIGS. 4A and 4B illustrate an access port connector 415 having a head shaped and dimensioned to be similar to the head shape and dimension of needle stem guards 430, 435, and 440. In this embodiment, manufacturing of only one interchangeable type of needle stem guard is possible.

FIG. 4A illustrates one embodiment of needle stick guard stems 430, 435, 440 deployed or positioned in an internal fluid pathway 425 to prevent the leaking out of fluid when a needle pricks or penetrates a flexible tubing 420 between an access port 405 and a gastric band (not shown). Each of the needle guard stems 430, 435, 440 may be identical. Furthermore, each of the needle guard stems 430, 435, 440 includes a barb or protrusion portion 433, 438 and 443, respectively, directed to block a portion of the internal fluid pathway 425 in order to prevent fluid passage from a joint to a puncture hole caused by a misdirected needle, thereby increasing the leaking prevention capabilities.

In addition, the needle guard stems 430, 435, 440 are slightly larger than the inner diameter of the internal fluid pathway 425 of the flexible tubing 420 and therefore press against the flexible tubing 420 to create a fluid seal.

FIG. 4B illustrates a close-up, cross-sectional view of FIG. 4A. As shown from left to right, an access port connector 415 defining a fluid conduit 450 may include a head 445 connectable to the first needle guard stem 430. More particularly, the head 445 fits into a tail portion 431 of the first needle guard stem 430. The first needle guard stem 430, in addition to the tail portion 431, may include a shaft portion 432, the barb portion 433 and a head 434 portion. The head portion 434 may fit into a tail portion 436 of the second needle guard stem 435 (in a manner that a ball may fit into a socket to create a flexible joint). The second needle guard stem 435 may also include a shaft portion 437, the barb portion 438 and a head portion 439. Similarly, the head portion 439 of the second needle guard stem 435 fits into the tail portion 441 of the third needle guard stem 440 to create another flexible joint. The third needle guard stem 440 may also include a shaft portion 442, the barb portion 443 and a head portion 444. The shaft portions 432, 437 and 442 may each be molded to include a cavity for transporting fluid through, for example, internal fluid pathways 451, 452 and 453 for establishing a fluid path between fluid conduit 450 and the internal fluid pathway 425.

The addition of the barb portions 433, 438 and 443 at the joint areas proximal to the location of the heads 434, 439 and 444 are located advantageously to prevent fluid passage from the joint to a punctured hole. For example, the barb portions 433, 438 and 443 function to provide protection to the joint from a misdirected needle. That is, the protruding aspects of the barb act as a shield to block the joint from being penetrated by a misdirected needle. In addition, since the barb portions 433, 438 and 443 significantly bulge out into the inner diameter of the tube, a better fluid seal is provided at the location of the barb portions 433, 438 and 443. In this manner, a leak may be limited to only existing fluid between two adjacent barbs since additional fluid cannot flow past the barbs and out of the puncture hole.

Certain embodiments have been disclosed to clarify the concepts including the above structural configurations. However, one skilled in the art will recognize that an endless number of implementations may be performed with the concepts herein. For example, the tube may be a catheter and may be used in other applications which require transferring fluid or gas.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A gastric banding system for the treatment of obesity, the gastric banding system comprising:
   an access port having an internal fluid reservoir and a conduit having a head;
   a gastric band having an inflatable portion;
   a tube having an inner surface, said inner surface defining a first pathway, the tube connecting the internal fluid reservoir to the inflatable portion; and
   a first stem guard located within the first pathway of the tube and configured to prevent a needle from passing therethrough, the first stem guard including:
   a first socket-shaped tail portion that receives the head of the conduit,
   a first ball-shaped head portion,
   a first shaft portion located between the first socket-shaped tail portion and the first ball-shaped head portion, the first shaft portion defining a second pathway for carrying fluid, and
   a first barb portion protruding from the first shaft portion and configured to extend into the inner surface of the tube.

2. The gastric banding system of claim 1 wherein an outer diameter of the first barb portion is greater than a diameter of the inner surface of the tube.

3. The gastric banding system of claim 2 further comprising:
   a second stem guard located within the first pathway of the tube, the second stem guard having:
   a second socket-shaped tail portion at a first end of the second stem guard for receiving the ball-shaped head portion of the first stem guard,
   a second ball-shaped head portion at a second end of the second stem guard,
   a second shaft portion continuing the second pathway between the first socket-shaped tail portion of the first stem guard and the second ball-shaped head portion of the second stem guard, the second pathway being coupled to a portion of the first pathway, and
   a second barb portion located between the second ball-shaped head portion and the second socket-shaped tail portion configured to block a portion of the first pathway between the second barb portion and the first barb portion while allowing fluid to pass through the second pathway.

4. The gastric banding system of claim 3 wherein a diameter of the second barb portion is greater than a diameter of the first pathway at the location of the second barb portion.

5. The gastric banding system of claim 4 further comprising:
   a third stem guard located within the first pathway of the tube, the third stem guard having:
   a third socket-shaped tail portion at a first end of the third stem guard for receiving the ball-shaped head portion of the second stem guard,
   a third ball-shaped head portion at a second end of the third stem guard,
   a third shaft portion continuing the second pathway between the first socket-shaped tail portion of the first stem guard and the third ball-shaped head portion of the third stem guard, the second pathway being coupled to a portion of the first pathway, and
   a third barb portion located between the third ball-shaped head portion and the third socket-shaped tail portion configured to block a portion of the first pathway between the third barb portion and the second barb portion while allowing fluid to pass through the second pathway.

6. The gastric banding system of claim 5 wherein a diameter of the third barb portion is greater than a diameter of the first pathway at the location of the third barb portion.

7. The gastric banding system of claim 5 wherein a flexible joint is created when the third socket-shaped tail portion receives the third ball-shaped head portion of the second stem guard.

8. The gastric banding system of claim 3 wherein a flexible joint is created when the second socket-shaped tail portion receives the ball-shaped head portion of the first stem guard.

9. The gastric banding system of claim 1 wherein a flexible joint is created when the first socket-shaped tail portion receives the head of the conduit.

10. A flexible tubing for carrying fluid between an access port and an inflatable portion of a gastric band, the flexible tubing comprising:
- a body configured to have a first end attachable to a bulbous end of a conduit of the access port and a second end attachable to the inflatable portion, the body having an inner surface, said inner surface defining a first pathway for carrying fluid; and
- a first stem guard located within the first pathway of the body and configured to prevent a needle from passing therethrough, the first stem guard including:
- a first socket-shaped tail portion constructed and sized to stably receive a bulbous end of the conduit,
- a first ball-shaped head portion,
- a first shaft portion located between the first socket-shaped tail portion and the first ball-shaped head portion, the first shaft portion defining a second pathway for carrying fluid, and
- a first barb portion protruding from the first shaft portion and configured to extend into the inner surface of the body.

11. The flexible tubing of claim 10 wherein a diameter of the first barb portion is greater than a diameter of the first pathway at the location of the first barb portion.

12. The flexible tubing of claim 10 wherein a flexible joint is created when the first socket-shaped tail portion receives the bulbous end of the conduit.

13. The flexible tubing of claim 10 further comprising:
- a second stem guard located within the first pathway of the body, the second stem guard having:
- a second socket-shaped tail portion for receiving the first ball-shaped head portion of the first stem guard,
- a second ball-shaped head portion,
- a second shaft portion located between the second socket-shaped tail portion and the second ball-shaped head portion, the second shaft portion further defining the second pathway for carrying fluid, and
- a second barb portion protruding from the second shaft portion and configured to extend into the inner surface of the body.

14. The flexible tubing of claim 13 wherein a diameter of the second barb portion is greater than a diameter of the first pathway at the location of the second barb portion.

15. The flexible tubing of claim 13 wherein a flexible joint is created when the second socket-shaped tail portion receives the ball-shaped head portion of the first stem guard.

16. A needle stem guard located internally within a first pathway of a flexible tubing for the prevention of leaks, the needle stem guard comprising:
- a socket-shaped tail portion constructed to receive and in engagement with a bulbous conduit connected to a fluid reservoir of an access port,
- a ball-shaped head portion,
- a shaft portion located between the socket-shaped tail portion and the ball-shaped head portion, the shaft portion defining a second pathway for carrying fluid, and
- a barb portion protruding from the shaft portion.

17. The needle stem guard of claim 16, wherein diameter of the barb portion is greater than a diameter of the first pathway at the location of the barb portion.

18. The needle stem guard of claim 16, wherein a flexible joint is created when the socket-shaped tail portion receives the bulbous conduit.

19. The needle stem guard of claim 16, wherein a distance between the socket-shaped tail portion and the ball-shaped head portion is 2.0 centimeters-4.0 centimeters.

20. The needle stem guard of claim 16, wherein the socket-shaped tail portion, the ball-shaped head portion, the shaft portion and the barb portion are all constructed out of biocompatible materials.

21. An access port for use with a gastric band for the treatment of obesity, the access port comprising:
(A) a housing enclosing a reservoir;
(B) a conduit having a first end connected to the reservoir and a bulbous second end;
(C) a tube with an inner surface, said inner surface defining a first pathway, said tube having a first end connected to the bulbous second end of the conduit and a second end connected to an inflatable portion of the gastric band; and
(D) a first stem guard located within the first pathway of the tube and constructed to prevent a needle with a normal application of force from passing therethrough, the first stem guard including:
(i) a first socket-shaped tail portion that receives the bulbous second end of the conduit,
(ii) a first ball-shaped head portion,
(iii) a first shaft portion located between the first socket-shaped tail portion and the first ball-shaped head portion, the first shaft portion defining a second pathway for carrying fluid, and
(iv) a first barb portion protruding from the first shaft portion and extending into the inner surface of the tube.

* * * * *